United States Patent [19]

Suzukamo et al.

[11] Patent Number: 4,485,257

[45] Date of Patent: Nov. 27, 1984

[54] PROCESS FOR PREPARING RACEMIZED CYCLOPROPANECARBOXYLIC ACIDS OR THEIR DERIVATIVES

[75] Inventors: Gohfu Suzukamo, Ibaraki; Masami Fukao, Shiga, both of Japan

[73] Assignee: Sumitomo Chemical Company, Limited, Osaka, Japan

[21] Appl. No.: 359,320

[22] Filed: Mar. 18, 1982

[30] Foreign Application Priority Data

Mar. 30, 1981 [JP] Japan .................................. 56-47818

[51] Int. Cl.$^3$ ........................ C07B 20/00; C07C 51/56
[52] U.S. Cl. ................................ 562/401; 260/544 L; 260/546; 562/506
[58] Field of Search ................. 260/546; 562/401, 506

[56] References Cited

U.S. PATENT DOCUMENTS 3,794,680  2/1974  Matsui et al. ....................... 562/401
3,989,750  11/1976  Nagase et al. .................. 260/544 L
4,182,906  1/1980  Suzukamo et al. ................. 562/506

*Primary Examiner*—Natalie Trousof
*Assistant Examiner*—Vera C. Clarke
*Attorney, Agent, or Firm*—Birch, Stewart, Kolasch & Birch

[57] ABSTRACT

The present invention is to provide the process for preparing racemized cyclopropanecarboxylic acids or their acid anhydrides from the corresponding optically active, particularly levo-rotatory, cyclopropanecarboxylic acid anhydrides. The racemization is effected by the treatment of the optically active acid anhydride with a Lewis acid. Thus, the present racemization process enables more efficient commercial production of dextro-rotatory cyclopropanecarboxylic acids, which are the more effective acid component of pyrethroidal insecticides, when combined with an optical resolution process.

8 Claims, No Drawings

PROCESS FOR PREPARING RACEMIZED CYCLOPROPANECARBOXYLIC ACIDS OR THEIR DERIVATIVES

The present invention relates to a process for preparing racemized cyclopropanecarboxylic acids or their derivatives. More particularly, it relates to a process for preparing racemized cyclopropanecarboxylic acids or their derivatives by treating optically active cyclopropanecarboxylic acid anhydrides as represented by the following formula (I),

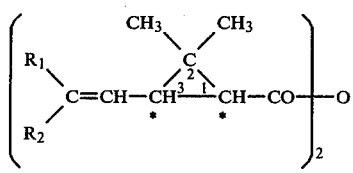

(wherein $R_1$ and $R_2$ designate a hydrogen atom, or an alkyl group having 1 to 4 carbons, or, when taken together with the carbon atom to which they are attached, represent a cycloalkylidene group having from 4 to 6 carbon atoms) with a Lewis acid to be subjected to the racemization, and obtaining the resulting racemized acid anhydrides as they are, or, alternatively, obtaining the racemized cyclopropanecarboxylic acids after the hydrolysis of the acid anhydrides.

The present invention also provides for a process for preparing racemized cyclopropanecarboxylic acids or their derivatives by converting optically active cyclopropanecarboxylic acids as represented by the following formula (II),

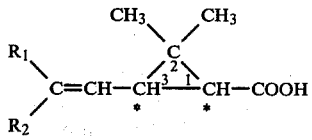

(wherein $R_1$ and $R_2$ have the same meanings as described above) to the corresponding optically active cyclopropanecarboxylic acid anhydrides as represented by the above formula (I), and then treating the resulting acid anhydrides in the similar way as mentioned above.

Among the cyclopropanecarboxylic acids as represented by the formula (II) described above, 2,2-dimethyl-3-(2-methyl-1-propenyl)cyclopropane-1-carboxylic acid is called chrysanthemic acid, and constitutes the acid component of the esters well-known as the so-called pyrethroidal insecticides, such as pyrethrin, allethrin, phthalthrin, etc., which are utilized as low toxic, quickly effective insecticides.

Besides, the cyclopropanecarboxylic acids such as 2,2-dimethyl-3-vinylcyclopropane-1-carboxylic acid, 2,2-dimethyl-3-cyclopentylidenemethylcyclopropane-1-carboxylic acid and 2,2-dimethyl-3-cyclohexylidenemethylcyclopropane-1-carboxylic acid, are also known as the acid components of pyrethroidal insecticides.

The cyclopropanecarboxylic acids represented by the above formula (II) have four kinds of isomers, that is, two geometrical isomers, i.e. cis and trans forms, which respectively have two kinds of optical isomers, i.e. (+) and (−) forms. It has been known that, in general, among the isomers the esters composed of a trans-form acid exhibit stronger insecticidal activity than those composed of a corresponding cis-form acid, and furthermore, the esters composed of a (+)-form acid exhibit exceedingly higher activity than those composed of the corresponding (−)-isomer.

In general, the cyclopropanecarboxylic acids of the above formula (II) are industrially produced as a mixture of cis and trans forms, each of which is in the form of a racemic modification, namely, as the (±)-form. The optical resolution of the thus-synthesized acids by means of an optically active organic base is conducted to obtain the (+)-form acids which are utilized for the preparation of insecticidal compounds with a high activity. The remaining (−)-isomers after the optical resolution are least useful, since the esters composed of them are almost inactive. Accordingly, it is a problem to be solved in the production of the (+)-form acids, particularly in a commercial scale, that the (−)-form acids be racemized with a high efficiency, so as to be utilized again as the material for the optical resolution mentioned above.

The racemization of the optically active cyclopropanecarboxylic acids represented by the formula (II) is highly difficult, since they possess two asymmetric carbon atoms, as shown above, at the 1- and 3-positions (exhibited by * marks). The transformation of the configuration solely at the $C_1$ asymmetric carbon atom, namely, the $C_1$-epimerization, is comparatively easier than the racemization. For such epimerization, there are known several methods as that a lower alkyl cis-chrysanthemate is heated in the presence of a specific basic catalyst to yield trans-chrysanthemic acid (Japanese Published Examined Patent Applications No. 18495/1978 and No. 18496/1978), and that cis-pyrethric acid chloride is heated at a high temperature (Japanese Published Examined Patent Application No. 24694/1971).

These methods are for the epimerization with respect to the $C_1$ asymmetric carbon, and by no means for the racemization to transform the configurations of both of the $C_1$ and $C_3$ asymmetric carbons.

On the other hand, some racemization methods have so far been studied. Thus, a method in which (−)-trans-chrysanthemic acid is oxidized at its $C_3$-substituted isobutenyl group to convert it into a keto-alcohol group, and the acid group at the $C_1$-position is converted into a lower alkyl ester, which is then subjected to a reaction with an alkali metal alcoholate in a solvent (Japanese Published Examined Patent Application No. 15977/1964); and a method in which (−)-trans-chrysanthemic acid is irradiated with ultraviolet rays in the presence of a photosensitizer (Japanese Published Examined Patent Application No. 30697/1972), have been known. In praticing these methods commercially, however, there remain various problems. The former method necessitates many reaction steps. In the latter method, the conversion is insufficient, with a large amount of electric power consumption of the illuminant, in addition to a comparatively short life of the illuminant.

Under such circumstances, the present inventors have conducted studies on efficient racemization processes for the said cyclopropanecarboxylic acids, and have previously found a process for racemization wherein an optically active cyclopropanecarboxylic acid halide is treated with a Lewis acid catalyst (U.S. Pat. Nos. 3,989,750 and 4,182,906).

After further studies on the highly efficient racemization process, the present inventors have now found that the optically active cyclopropanecarboxylic acid anhydrides of the formula (I) can be racemized conveniently by the treatment with a Lewis acid. Thus, the present invention has been accomplished based upon these findings with the various additional investigations.

The process of the present invention will more fully be described hereinafter. The carboxylic acid anhydrides represented by the formula (I) may easily be derived from the corresponding carboxylic acids represented by the general formula (II), according to such methods as (i) direct dehydration of the acid with acetic acid anhydride or acetyl chloride, (ii) reaction of a salt of the acid with a halide of the acid, and (iii) dehydrogen chloride reaction between the acid and a halide of the acid in the presence of a base. The racemization of the resulting acid anhydrides readily proceeds by the treatment with a Lewis acid, such as iodine, or metal halide type Lewis acid, for example, tin tetrachloride, iron chloride, aluminum chloride, aluminum bromide, titanium chloride, zinc chloride or the like, and the complex compounds thereof, irrespective of the external pressure. Among these Lewis acids, iodine gives more favorable results.

The starting optically active carboxylic acid may be any of four optical isomers solely, or may be a mixture of them in an arbitrary proportion. The acid material of any degree of optical purity may be employed. Needless to say, however, employment of the carboxylic acids of (−)-form, or rich in (−)-form, i.e. levo-rotatory acids, makes the object of the present invention significant.

In carrying out the present racemization reaction, a solvent may preferably be used, which is inert to the racemization reaction substantially. For such solvents, there may be illustrated ethers, aromatic hydrocarbons and their halide compounds, other hydrocarbons and their halide compounds, etc.

The Lewis acid may be used in an amount of about 1/1000 to ½ mol, preferably about 1/200 to 1/5 mol, based upon a mol of the acid anhydride to be treated.

The reaction temperature may generally be chosen arbitrarily within the range from about −50° C. to the boiling point of the acid anhydride used (or the boiling point of the solvent if used), preferably from about −20° to 150° C.

The reaction time is more or less associated with the amount of Lewis acid and the reaction temperature. Usually the object would be well achieved within a period of time ranging from about 10 minutes to 20 hours.

The racemized carboxylic acid anhydride thus-prepared may be reacted with a pyrethroidal alcohol, for example, pyrethrolone and allethrolone, to produce an insecticidal ester. Alternatively, it may be once converted to the corresponding acid halide with a halogenating agent such as thionyl chloride, and the resulting acid halide is then reacted with the said alcohol, to obtain the same insecticidal ester.

Upon hydrolysis of the racemized acid anhydride by addition of an aqueous alkali solution according to the conventional procedure, the corresponding racemized carboxylic acid is readily obtained, which may be employed as the starting material to prepare its (+)-isomer through the optical resolution as mentioned above, or to produce an insecticidal ester.

As described, the process of the present invention enables the transformation of the cyclopropanecarboxylic acids represented by the general formula (II), which are of, or rich in, (−)-form, namely levo-rotatory, into the useful racemized cyclopropanecarboxylic acid in a commercial scale with a high efficiency. Moreover, the combination of the process of the invention with the process of the optical resolution enables the conversion of the (−)-form carboxylic acids into the useful (+)-form carboxylic acids. Thus, it can be said that the present invention is very useful in the field of pyrethroidal insecticides.

Also, the racemic cyclopropanecarboxylic acids or acid anhydrides obtained according to the process of the present invention is rich in the trans-form which is more useful for the preparation of insecticidal esters. This fact constitutes an additional advantage of the process of the invention.

The method of the present invention will be further illustrated in the following examples, which, however, should not be construed to be limitative.

EXAMPLE 1

In a 500 ml flask were placed 200 g of toluene, 27.8 g of (−)-trans-2,2-dimethyl-3-isobutenylcyclopropane-1-carboxylic acid chloride and 25.0 g of (−)-trans-2,2-dimethyl-3-isobutenylcyclopropane-1-carboxylic acid. Into the mixture was added drop-wise 11.9 g pyridine, while stirring under nitrogen at a temperature of 20° to 25° C. After 5 hours, the reaction mixture was washed sequentially with an aqueous 10% hydrogen chloride solution, an aqueous 5% sodium hydroxide solution, and water, and then concentrated in vacuo. The residue was distilled in vacuo at boiling point 130° to 135° C./0.2 mmHg, to obtain 46.1 g of (−)-trans-2,2-dimethyl-3-isobutenylcyclopropane-1-carboxylic acid anhydride, with $[\alpha]_D - 17.3°$ (C=1, $CH_2Cl_2$).

EXAMPLE 2

Using 55.5 g of a levo-rotatory 2,2-dimethyl-3-isobutenylcyclopropane-1-carboxylic acid chloride and 50.0 g of a levo-rotatory 2,2-dimethyl-3-isobutenylcyclopropane-1-carboxylic acid [the both having the constitution of 3.3% of (+)-cis, 19.8% of (−)-cis, 11.7% of (+)-trans, and 65.2% of (−)-trans isomers], with otherwise the similar procedure as in Example 1, 90.6 g of levo-rotatory 2,2-dimethyl-3-isobutenylcyclopropane-1-carboxylic acid anhydride was prepared, with the boiling point 158° to 168° C./0.3 mmHg.

EXAMPLE 3

Into a 500 ml flask equipped with a distillation apparatus, were placed 113 g of a levo-rotatory 2,2-dimethyl-3-isobutenylcyclopropane-1-carboxylic acid [having the constitution of 2.2% of (+)-cis, 20.6% of (−)-cis, 10.2% of (+)-trans and 67.0% of (−)-trans isomers] and 275 g of acetic anhydride. The mixture was heated to distill the resulting acetic acid off until the distilling temperature reached 133° C. Then the residue was distilled in vacuo (0.3 to 0.4 mmHg) to obtain 104.8 g of the corresponding levo-rotatory acid anhydride.

EXAMPLE 4

Into a 100 ml reaction vessel replaced with nitrogen atmosphere, were placed 15.0 g of (−)-2,2-dimethyl-3-isobutenylcyclopropane-1-carboxylic acid anhydride (prepared in Example 1) and 35 g of toluene. To the mixture was added 1.02 g of iodine, followed by stirring at a temperature of 70° C. for 60 minutes. The reaction mixture was analyzed for the ratio of the optical isomers by means of gas chromatography. The results showed the progress of racemization, as follows: 5.4% of (+)-cis, 4.3% of (−)-cis, 43.4% of (+)-trans and 46.9% of (−)-trans isomer.

Then the reaction mixture was concentrated to remove the toluene off to give the remainder racemized acid anhydride. To this was added 25 g of an aqueous 20% sodium hydroxide solution, and the mixture was stirred at a temperature of 80° C. for 3 hours. The reaction mixture was extracted with toluene to remove the impurities, and the aqueous layer was acidified with an aqueous 20% sulfuric acid and then extracted with toluene. The toluene layer was washed with water, and then evaporated to remove the toluene. The residue was distilled at boiling point 95° to 104° C./0.2 mmHg to give 12.75 g of the corresponding racemized carboxylic acid, which readily crystallized (melting point 48° to 52° C.). Its infrared spectrum was identified with that of (±)-2,2-dimethyl-3-isobutenyl cyclopropane-1-carboxylic acid.

EXAMPLE 5

In a 100 ml reaction vessel replaced with nitrogen atmosphere, were charged 15.0 g of the levo-rotatory acid anhydride (prepared in Example 2) and 35 g of toluene. To the mixture was added 1.0 g of iodine. The mixture was stirred at a temperature of 70° C. for 60 minutes. During the course of the reaction, a part of the reaction mixture was sampled at intervals, chlorinated with thionyl chloride and analysed by gas chromatography. The results are as follows.

| Time (minute) | Ratio of optical isomers (%) | | | |
|---|---|---|---|---|
| | (+)-cis | (−)-cis | (+)-trans | (−)-trans |
| 0 (Starting material) | 3.8 | 17.9 | 11.6 | 66.7 |
| 10 | 5.8 | 4.6 | 37.1 | 52.5 |
| 30 | 5.2 | 4.0 | 43.0 | 47.8 |
| 60 | 5.2 | 3.9 | 44.4 | 46.5 |

The reaction mixture was concentrated to obtain the acid anhydride, which was then hydrolyzed in the similar way as in Example 4. The resulting racemized carboxylic acid had melting point of 48° to 52° C.

EXAMPLE 6

In a 200 ml reaction vessel were placed 10.3 g of the levo-rotatory carboxylic acid anhydride (prepared in Example 2) and 90 g of dioxane. To the mixture was added 1.02 g of ferric chloride. The mixture was stirred at a temperature of 70° C. for 60 minutes. The ratio of the optical isomers in the reaction mixture was as follows, showing the progress of racemization.

(+)-cis: 3.1%
(−)-cis: 3.4%
(+)-trans: 41.8%
(−)-trans: 51.8%

A small amount of water was added to the reaction mixture to decompose the ferric chloride. After removal of the decomposed iron compound, the reaction mixture was hydrolyzed in the same way as in Example 4, to obtain 6.71 g of the corresponding racemized carboxylic acid having boiling point 95° to 104° C./0.2 mmHg.

EXAMPLE 7

In a 200 ml reaction vessel were charged 10.0 g of the levo-rotatoy acid anhydride (prepared in Example 3) and 90 g of toluene. While cooling, 1.67 g of tin tetrachloride was added to the mixture. The mixture was stirred at a temperature of 50° C. for 3 hours. A part of the reaction mixture was sampled and analyzed, with the optical isomer ratio of 1.3% of (+)-cis, 1.5% of (−)-cis, 43.1% of (+)-trans and 54.1% of (−)-trans forms.

EXAMPLE 8

In a 500 ml reaction vessel replaced with nitrogen atmosphere, were charged 20.0 g of the levo-rotatory acid anhydride prepared in Example 3, and 180 g of toluene. Into the mixture was added 3.35 g of aluminum chloride. The mixture was stirred at a temperature of 100° C. for 7 hours. A part of the reaction mixture was sampled and analyzed, with the results of 4.0% of (+)-cis, 6.7% of (−)-cis, 40.5% of (+)-trans and 48.7% of (−)-trans forms.

We claim:

1. A process for preparing racemized cyclopropanecarboxylic acid anhydrides, which comprises treating an optically active cyclopropanecarboxylic acid anyhdride as represented by the following formula,

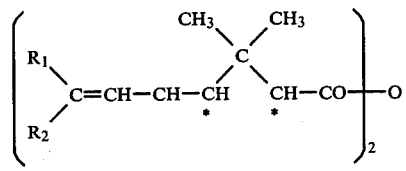

wherein $R_1$ and $R_2$, respectively, designate a hydrogen atom or an alkyl group having 1 to 4 carbons, or, when taken together with the carbon atom to which they are attached, represent a cycloalkylidene group consisting of from 4 to 6 carbon atoms, with iodine in the presence or absence of an inert solvent at a temperature of from about −50° C. to the boiling point of the reaction system.

2. A process for preparing racemized cyclopropanecarboxylic acids, which comprises treating an optically active cyclopropanecarboxylic acid anhydride as represented by the following formula,

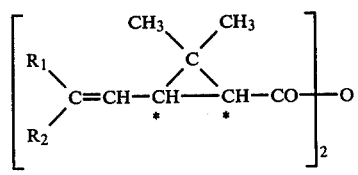

wherein $R_1$ and $R_2$, respectively, designate a hydrogen atom or an alkyl group having 1 to 4 carbons, or, when taken together with the carbon atom to which they are attached, represent a cycloalkylidene group consisting of from 4 to 6 carbon atoms, with iodine in the presence or absence of an inert solvent at a temperature of from about −50° C. to the boiling point of the reaction system, and hydrolyzing the treated mixture to obtain the corresponding racemized cyclopropanecarboxylic acid.

3. A process for preparing racemized cyclopropanecarboxylic acid anhydrides, which comprises converting an optically active cyclopropanecarboxylic acid as represented by the following formula,

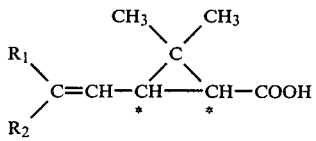

wherein $R_1$ and $R_2$ respectively designate a hydrogen atom or an alkyl group having 1 to 4 carbons, or, when taken together with the carbon atom to which they are attached, represent a cycloalkylidene group consisting of from 4 to 6 carbon atoms, into the corresponding optically active cyclopropanecarboxylic acid anhydride represented by the following formula,

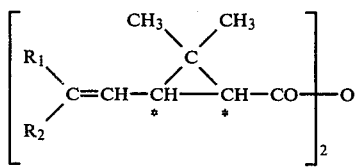

wherein $R_1$ and $R_2$ have the same meanings as above, and treating the optically active acid anhydride with iodine in the presence or absence of an inert solvent at a temperature of from about $-50°$ C. to the boiling point of the reaction system.

4. A process for preparing racemized cyclopropanecarboxylic acids, which comprises converting an optically active cyclopropanecarboxylic acid represented by the following formula,

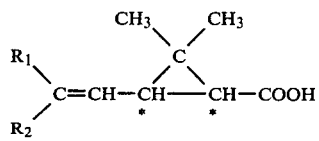

wherein $R_1$ and $R_2$, respectively, designate a hydrogen atom or an alkyl group having 1 to 4 carbons, or, when taken together with the carbon atom to which they are attached, represent a cycloalkylidene group consisting of from 4 to 6 carbon atoms, into the corresponding optically active cyclopropanecarboxylic acid anhydried represented by the following formula,

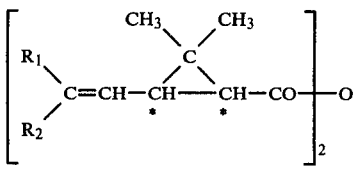

wherein $R_1$ and $R_2$ have the same meanings as above, treating the optically active acid anhydride with iodine in the presence or absence of an inert solvent at a temperature of from about $-50°$ C. to the boiling point of the reaction system, and hydrolyzing the treated mixture to obtain the corresponding racemized cyclopropanecarboxylic acid.

5. The process according to any one of claims 1, 2, 3 or 4, wherein the reaction temperature is from about $-20°$ to $150°$ C.

6. The process according to any one of claims 1, 2, 3, or 4, wherein the treatment with iodine is effected in an inert solvent.

7. The process according to claim 6, wherein the inert solvent is selected from the group consisting of ethers, aromatic hydrocarbons, halogen substituted aromatic hydrocarbons, aliphatic hydrocarbons and halogen substituted aliphatic hydrocarbons.

8. The process according to any one of claims 1, 2, 3 or 4, wherein the amount of iodine is about 1/1000 to ½ mol based on the acid anhydride.

* * * * *